US012438349B2

(12) United States Patent
Alvarez

(10) Patent No.: US 12,438,349 B2
(45) Date of Patent: Oct. 7, 2025

(54) SMART IV POLE

(71) Applicant: Angel Medical LLC, Dover, DE (US)

(72) Inventor: Gabriel G. Alvarez, Pinecrest, FL (US)

( * ) Notice: Subject to any disclaimer, the term of this patent is extended or adjusted under 35 U.S.C. 154(b) by 262 days.

(21) Appl. No.: 18/132,099

(22) Filed: Apr. 7, 2023

(65) Prior Publication Data

US 2023/0335978 A1 Oct. 19, 2023

Related U.S. Application Data

(60) Provisional application No. 63/330,347, filed on Apr. 13, 2022.

(51) Int. Cl.

| | |
|---|---|
| ***H02G 3/08*** | (2006.01) |
| ***A61B 50/22*** | (2016.01) |
| ***A61B 50/26*** | (2016.01) |
| ***F16M 11/04*** | (2006.01) |
| ***F16M 11/42*** | (2006.01) |
| ***H02G 11/02*** | (2006.01) |
| *H02J 9/06* | (2006.01) |

(52) U.S. Cl.
CPC ............... *H02G 3/08* (2013.01); *A61B 50/22* (2016.02); *A61B 50/26* (2016.02); *F16M 11/045* (2013.01); *F16M 11/046* (2013.01); *F16M 11/42* (2013.01); *H02G 11/02* (2013.01); *H02J 9/06* (2013.01)

(58) Field of Classification Search
CPC .......... H02G 3/08; H02G 11/02; A61B 50/22; A61B 50/26; F16M 11/045; F16M 11/046; F16M 11/42; H02J 9/06
USPC .......................................................... 361/622
See application file for complete search history.

(56) References Cited

U.S. PATENT DOCUMENTS 4,756,706 A * 7/1988 Kerns .................. A61M 5/142 128/DIG. 13
4,807,837 A * 2/1989 Gawlik ............... A61M 5/1415 211/196
4,898,578 A * 2/1990 Rubalcaba, Jr. ...... A61M 5/172 700/83
5,344,169 A * 9/1994 Pryor .................. A61G 12/008 5/503.1
5,527,289 A 6/1996 Foster et al.
5,890,687 A * 4/1999 Pryor ................. A61M 5/1415 280/42

(Continued)

FOREIGN PATENT DOCUMENTS

EP 3192538 B1 3/2020
WO WO-9927818 A1 * 6/1999 ........... A61G 12/002

*Primary Examiner* — Anatoly Vortman
(74) *Attorney, Agent, or Firm* — Barry Choobin; Patent 360

(57) ABSTRACT

A smart IV pole is provided for supporting a variety of equipment utilized by the anesthesiology care team and critical care staff. The smart IV pole includes a lower section, a middle section affixed to the lower section, and an adjustable upper section movably mounted to the middle section. The lower section includes a transport base, an uninterrupted power supply and cover mounted on the transport base, and a retractable cable reel in the base. The middle section includes a plurality of pivotable infusion pump arms. The adjustable upper section includes a plurality of hooks for suspending solution bags. The smart IV pole additionally includes a rail on the transport base, an auxiliary tray, and a blood reservoir.

16 Claims, 8 Drawing Sheets

(56) References Cited

U.S. PATENT DOCUMENTS

| | | | | |
|---|---|---|---|---|
| 6,626,445 | B2 | 9/2003 | Murphy | |
| 7,154,397 | B2 * | 12/2006 | Zerhusen | A61G 7/0507 340/286.07 |
| 9,290,196 | B1 * | 3/2016 | Siegel | B62B 5/049 |
| 11,627,212 | B2 * | 4/2023 | Hatch | G08B 25/08 361/679.01 |
| 2002/0096608 | A1 * | 7/2002 | Cedarberg, III | A61M 5/1418 248/68.1 |
| 2005/0000019 | A1 | 1/2005 | Newkirk et al. | |
| 2005/0116126 | A1 * | 6/2005 | Ugent | A61M 5/1415 248/129 |
| 2007/0221796 | A1 | 9/2007 | Silverman et al. | |
| 2007/0267550 | A1 * | 11/2007 | Blankenship | A61G 12/008 248/161 |
| 2008/0234555 | A1 * | 9/2008 | Lafleche | A61B 5/00 600/300 |
| 2008/0283692 | A1 * | 11/2008 | Leinen | A61M 5/1415 248/129 |
| 2011/0174936 | A1 * | 7/2011 | Cox | A61B 50/13 248/163.1 |
| 2015/0224256 | A1 * | 8/2015 | Lee | A61M 5/1411 604/67 |
| 2015/0327936 | A1 * | 11/2015 | Coleman | A47B 81/00 211/85.13 |
| 2016/0000995 | A1 * | 1/2016 | Blankenship | A61M 5/1415 248/514 |
| 2016/0157951 | A1 * | 6/2016 | Schoenig | F16M 11/38 280/47.35 |
| 2017/0361014 | A1 * | 12/2017 | Koehler | A61M 5/1415 |

* cited by examiner

SMART IV POLE

CROSS-REFERENCE TO RELATED APPLICATIONS

This patent application claims the benefit of U.S. Provisional Patent Application Ser. No. 63/330,347 filed Apr. 13, 2022, which is incorporated herein by reference thereto.

FIELD OF THE INVENTION

The present invention generally relates to medical intravenous infusion IV poles, and, more particularly, to a smart IV pole as a structure to provide an uninterrupted electrical power supply and a centralized location to support and organize various equipment utilized in the care of critically ill patients.

BACKGROUND OF THE INVENTION

Anesthesiologist and critical care staff often require a large amount of equipment readily on hand to perform their duties attending to critically ill patients. Such equipment may include multiple drug infusion pumps, fluid warming devices, massive transfusion sets, hot air blower devices, solution bags for blood or other intravenous solutions and the like.

A common way of securing the various equipment is on a single intravenous or IV pole. These are typically vertical telescoping poles mounted at the bottom center of multiple long branched legs radiating outward with exposed wheels. These spoke-like legs may be independent or interlinked, forming a large base with wide gaps. These bases take up a substantial amount of room circumferentially with a fixed broad footprint in all environments the IV poles are used, conflicting with other standing equipment within a limited space. In the operating room theater, the IV pole legs collide with the anesthesia machine, blood cell saver processing machine, and ultrasound machine, among others. The problem is compounded when several IV poles are required to mount additional equipment for the care of complex surgery like open heart surgery, organ transplant or life-saving equipment for trauma patients. During transport of the critical ill patient from the operating room to the Intensive Care Unit, the long radiating legs bang against the ICU bed wheels and other equipment routinely stationed on the narrow hallways of all hospitals. Lastly, the ICU room may have limited floor space due to an increase use of newer continuous monitoring equipment that requires an independent standing support tower.

All the medical devices that may be attached to the lower section of the IV pole or as a stand-alone equipment in the operating room theater have an electrical power cords of 5 to 10 feet long. These are medically graded cords that despite conscious care by the personnel, they keep uncoiled, detached, tangled, kink or crushed by the heavy equipment including the IV pole when is fully loaded. The expose wheels of each of the legs are inoperative when surrounded by entangled cables on the floor, impeding any translational movement of the IV pole for an alternative position. Depending on the number of drug infusion pumps attached to the IV pole, there may be insufficient electrical outlets near available having the need to run power cords "floating" through the air to the next medically graded electrical wall outlet creating a safety hazard for the personnel.

The majority of IV poles are a single two part telescoping vertical tubes often too small in diameter and fragile to hold, secure or support multiple heavy medical devices at once. Others sturdiest IV poles have a "fork" type structure or "Y" shape with 90-degree angles holding vertical fixed poles increasing the space to secure more medical devices including multiple drug infusion pumps. Nevertheless, when more drug infusion pumps are needed than the capacity of these two vertical poles, additional horizontal plates have to the added as extension accessories which causes conflict between them and weight-balance problems especially at transportation.

Additionally, the continuous operation of the medical equipment in the operating room and intensive care unit is often critical to the clinical state and safety of the patient. These not only include the drug infusion pumps but the anesthesia machine, computers supporting ancillary function and vital respirators. Any disruption of power, even for just several seconds while the Hospital generator is activated, causes the various medical equipment to rebut compromising patient safety, with exponential risk when having extended power plant failures that have been reported.

Lastly, there is no consistency in inventory control, location, and positioning of the medical equipment needed for the care of the critically ill patient in the perioperative period, meaning from the pre-surgical suite, the operating room theater, and the recovery room or intensive care unit. Some of the essential medical equipment is attached to IV poles, and others are as a standalone in any of these rooms, which causes delays in patient management if they are not centralized.

Accordingly, there is a need for a solution to at least one of the aforementioned problems. For instance, there is an established need for an IV pole that can reliably provide an uninterrupted power supply to a large variety of medical equipment mounted in a centralized structure.

SUMMARY OF THE INVENTION

The present invention is directed to a smart IV pole for supporting a variety of equipment utilized by the anesthesiology care team and critical care staff. The smart IV pole includes a lower section, a middle section coupled to the lower section, and an adjustable upper section. The lower section includes a transport base with a mounted cover, an uninterrupted power supply, and a retractable cable reel housed in the base to provide a bottom-exiting electrical plug. The middle section includes a plurality of pivotable infusion pump arms carried by a carrier subassembly. The pivotable arms can be equipped with charging ports to enable cable-free installation and operation of the infusion pumps. An exemplary frame structure includes a pair of vertical supporting poles to support the middle section relative to the lower section. The adjustable upper section includes a length-adjustable vertical portion and a length-adjustable horizontal portion disposed at the upper end of the vertical portion. The horizontal portion includes a plurality of hooks to suspend solution bags. The plug of a retractable electrical cord is threaded through the vertical portion and emerges as a top-exiting component available for plug-in to a ceiling outlet. The smart IV pole additionally includes a retention rail at the base to secure and protect equipment. The smart IV pole includes sensors for medical device location system for the equipment installed.

In an exemplary implementation of the invention, a stand assembly comprises:

a base subassembly;

a carrier subassembly disposed above the base subassembly; and an arm subassembly mounted to the carrier subassembly and including one or more arms pivotably connected to the carrier subassembly.

In a second aspect, at least one arm of the arm subassembly is configured to selectably adopt a deployed configuration and a retracted configuration.

In another aspect, at least one arm of the arm subassembly is configured in a first mode to pivot about a generally horizontal axis enabling the arm to traverse through a generally vertical plane, and configured in a second mode to pivot about a generally vertical axis enabling the arm to traverse through a generally horizontal plane.

In another aspect, the first mode facilitates retraction of the arm into a generally vertical orientation and facilitates extension of the arm into a generally horizontal orientation.

In another aspect, the assembly further includes a container-supporting rack subassembly. The rack subassembly includes, in combination, a proximal end coupled to the base subassembly, a distal end, a length-adjustable generally vertical first portion extending between the proximal end and the distal end, and a length-adjustable generally horizontal second portion disposed at the distal end.

In another aspect, the rack subassembly further includes, in combination, an adjustable first telescoping device defining at least part of the first portion of the rack subassembly; a pair of independently adjustable second telescoping devices defining at least part of the second portion of the rack subassembly and extending in opposite directions; and at least one hook disposed on the second portion of the rack subassembly.

In another aspect, the base subassembly further includes, in combination, a wheeled unit, and a cover configured to cover the wheeled unit. The cover includes an upper side and a sloping lateral structure extending from the upper side and having a lower peripheral edge.

In another aspect, the assembly further includes a brake system configured to apply a braking action to the base subassembly. The cover includes a front opening formed in the lateral structure of the cover to enable access to the brake system.

In another aspect, the brake system further includes, in combination, a brake element; and, a user-actuatable mechanism configured to move the brake element between a braking position in which the brake element is disposed in contacting engagement with a ground surface, and a release position in which the brake element is disengaged from the ground surface.

In another aspect, at least one arm of the arm subassembly includes one or more charging ports.

In another aspect, the assembly further includes one or more mounting brackets each incorporating a respective one of the one or more charging ports and configured to define a device mounting structure disposed on the arm subassembly.

In another aspect, the assembly further includes a device configured to provide an indication of a location of the assembly. The assembly adopts a loading configuration in which one or more medical devices mounts to one or more arms of the arm subassembly. The assembly further includes at least one location indicator each associated with a respective one of the one or more medical devices mounted to the one or more arms of the arm subassembly.

In another aspect, the assembly further includes an electrical subassembly. The electrical subassembly includes, in combination, one or more charging ports disposed on the arm subassembly, one or more electrical outlets disposed on the base subassembly and/or the carrier subassembly, one or more mobile device connectors disposed on the base subassembly and/or the carrier subassembly, one or more retractable power cable reels each housed in the assembly and having an input plug available to connect to an external power source and an output plug, an uninterruptible power supply, and a power distribution circuit configured to electrically couple the uninterruptible power supply and/or the one or more retractable power cable reels to the one or more charging ports, the one or more electrical outlets, and the one or more mobile device connectors.

In another aspect, the base subassembly includes, in combination, a wheeled unit, and a cover configured to cover the wheeled unit. The cover includes an upper side and a sloping sidewall structure extending from the upper side. At least one arm of the arm subassembly is configured to selectably adopt a deployed configuration and a retracted configuration. Additionally, at least one arm of the arm subassembly includes one or more charging ports.

In another aspect, the base subassembly includes, in combination, a wheeled unit, and a cover configured to cover the wheeled unit. The cover includes an upper side and a sloping foot structure extending from the upper side. At least one arm of the arm subassembly is configured to pivot about a generally horizontal axis enabling the arm to traverse through a generally vertical plane and to move between a retracted position and an extended position, and further configured to pivot about a generally vertical axis enabling the arm to traverse through a generally horizontal plane. At least one arm of the arm subassembly includes one or more charging ports. The assembly further includes one or more mounting brackets each incorporating a respective one of the one or more charging ports and configured to define a device mounting structure disposed on the arm subassembly.

In another aspect, the base subassembly includes, in combination, a wheeled unit, a brake system configured to apply a braking action to the base subassembly, and a cover configured to cover the wheeled unit and at least part of the brake system. The cover includes an upper side, a sloping sidewall structure extending from the upper side, and a front opening formed in the sidewall structure to enable access to the brake system. At least one arm of the arm subassembly is configured to pivot about a generally horizontal axis enabling the arm to traverse through a generally vertical plane and to move between a retracted position and an extended position, and further configured to pivot about a generally vertical axis enabling the arm to traverse through a generally horizontal plane. Additionally, at least one arm of the arm subassembly includes one or more charging ports. The assembly further includes one or more mounting brackets each incorporating a respective one of the one or more charging ports and configured to define a device mounting structure disposed on the arm subassembly. A device is configured to provide an indication of a location of the assembly. The assembly adopts a loading configuration in which one or more medical devices mounts to one or more arms of the arm subassembly via the one or more mounting brackets. The assembly further includes at least one location indicator each associated with a respective one of the one or more medical devices mounted to the one or more arms of the arm subassembly.

In another aspect, the base subassembly includes, in combination, a wheeled unit, a brake system configured to apply a braking action to the base subassembly, and a cover configured to cover the wheeled unit and at least part of the brake system. The cover includes an upper side, a sloping sidewall structure extending from the upper side, and a front opening formed in the sidewall structure to enable access to the brake system. At least one arm of the arm subassembly is configured to selectively pivot and adopt a deployed configuration and a retracted configuration. The assembly further includes a rack arrangement, which comprises, in combination, a proximal end coupled to the base subassembly, a distal end, a length-adjustable generally vertical first portion extending between the proximal end and the distal end, and a length-adjustable generally horizontal second portion disposed at the distal end.

In another aspect, the assembly further includes an electrical subassembly. The electrical subassembly includes, in combination, one or more charging ports disposed on the arm subassembly, one or more electrical outlets disposed on the base subassembly and/or the carrier subassembly, one or more mobile device connectors disposed on the base subassembly and/or the carrier subassembly, one or more retractable power cable reels each having an input plug available to connect to an external power source and an output plug, an uninterruptible power supply, and a power distribution circuit configured to electrically couple the uninterruptible power supply and/or the one or more retractable power cable reels to the one or more charging ports, the one or more electrical outlets, and the one or more mobile device connectors.

These and other objects, features, and advantages of the present invention will become more readily apparent from the attached drawings and the detailed description of the preferred embodiments, which follow.

BRIEF DESCRIPTION OF THE DRAWINGS

The preferred embodiments of the invention will hereinafter be described in conjunction with the appended drawings provided to illustrate and not to limit the invention, where like designations denote like elements, and in which.

Like reference numerals refer to like parts throughout the several views of the drawings.

DETAILED DESCRIPTION

The following detailed description is merely exemplary in nature and is not intended to limit the described embodiments or the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to make or use the embodiments of the disclosure and are not intended to limit the scope of the disclosure, which is defined by the claims. For purposes of description herein, the terms "upper", "lower", "left", "rear", "right", "front", "vertical", "horizontal", and derivatives thereof shall relate to the invention as oriented in FIG. 1. Furthermore, there is no intention to be bound by any expressed or implied theory presented in the preceding technical field, background, brief summary or the following detailed description. It is also to be understood that the specific devices and processes illustrated in the attached drawings, and described in the following specification, are simply exemplary embodiments of the inventive concepts defined in the appended claims. Hence, specific dimensions and other physical characteristics relating to the embodiments disclosed herein are not to be considered as limiting, unless the claims expressly state otherwise.

The phrase "and/or," as used herein, should be understood to mean "either or both" of the elements so joined, i.e., elements that are conjunctively presented in some cases and disjunctively presented in other cases.

As used herein, an element or step recited in the singular and proceeded with the word "a" or "an" should be understood as not excluding plural elements or steps, unless such exclusion is explicitly recited.

Shown throughout the figures, the present invention is directed toward a smart intravenous pole assembly for use in supporting, carrying and safely organizing various items of medical equipment and supplies utilized in a treatment setting or health care environment, such as an operating room theater and/or workstation of a critical care unit.

Figure 1:
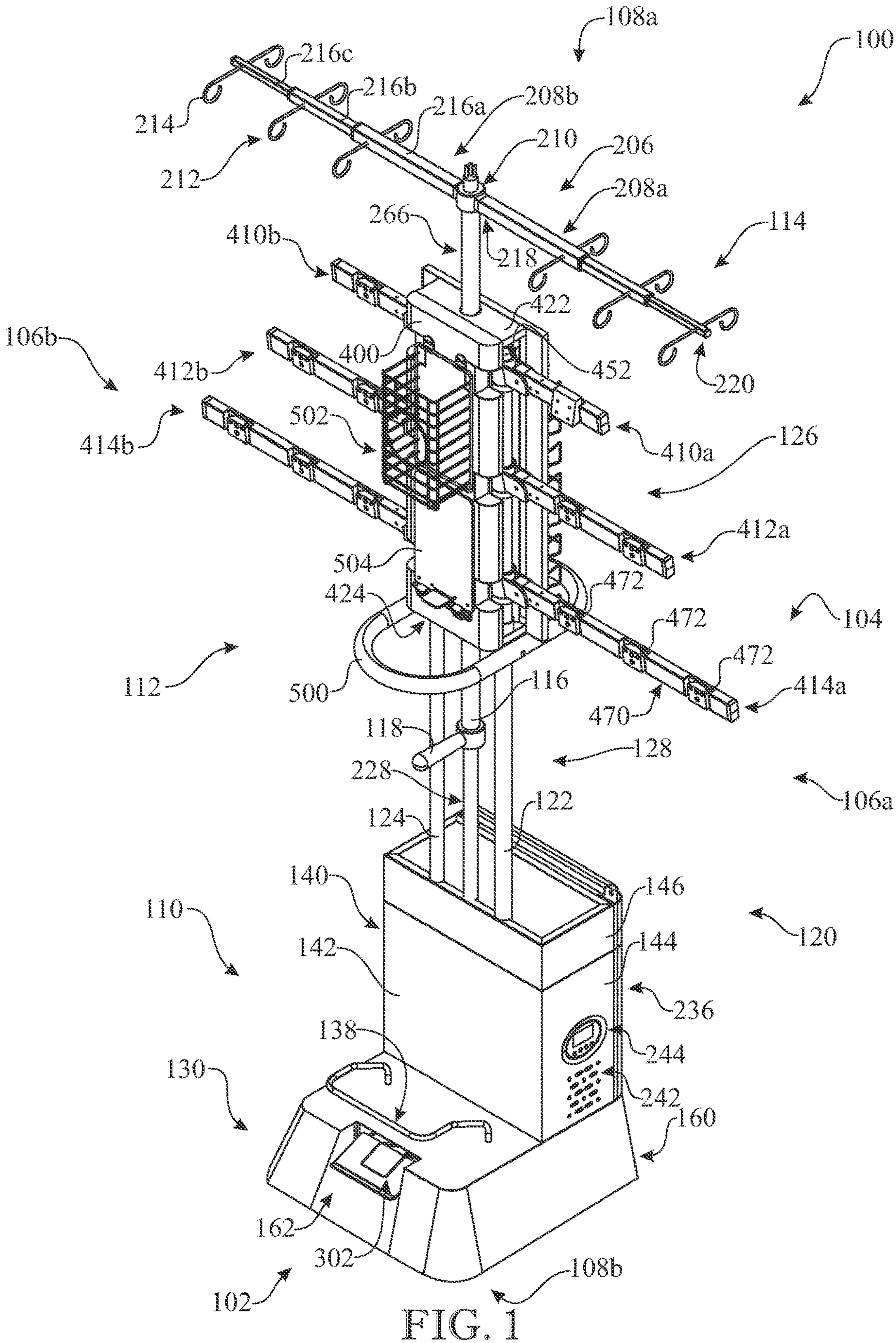
FIG. 1 presents a front, upper, right-side isometric view of an intravenous pole assembly for use in patient care settings and showing a set of retractable horizontal support arms in their extended position, in accordance with a first illustrative embodiment of the present invention.
Figure 2:
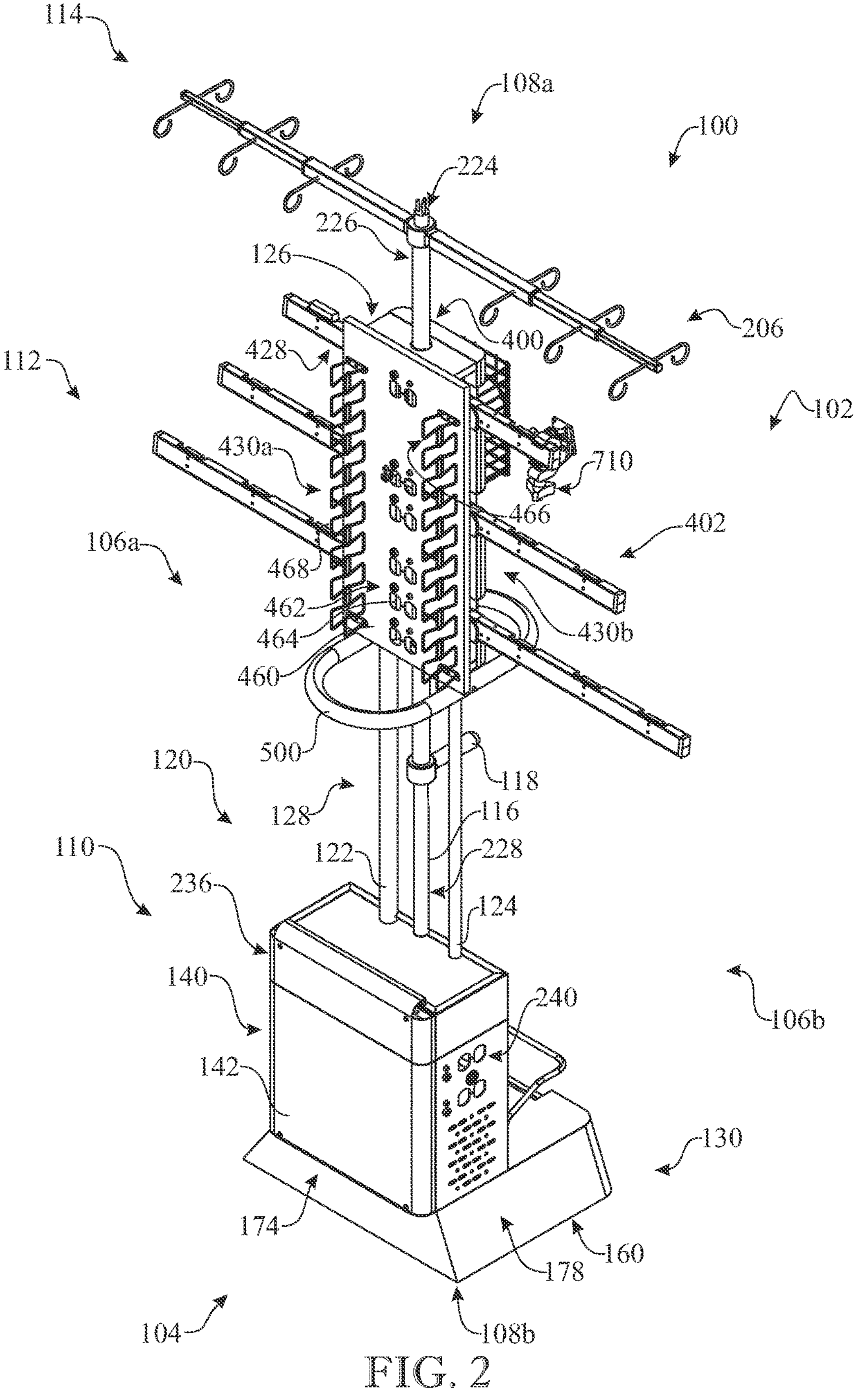
FIG. 2 presents a rear, upper, left-side isometric view of the intravenous pole assembly illustrated in FIG. 1.

Referring initially to FIGS. 1-2, a standalone, smart intravenous ("IV") pole or tower assembly, hereinafter assembly 100, is illustrated in accordance with an exemplary embodiment of the present invention. The illustrated assembly 100 is shown in its upright, deployed, operation-ready configuration. The assembly 100, in one form, is configured as an erect, standing structure having a variable-sized, multi-rack arrangement configured to mount and power various medical devices (e.g., IV infusion pumps), and to hang and support various medical supplies (e.g., fluid bags). The assembly 100 can be self-powering (e.g., onboard, resident power supply) and/or powered by connection to an external power source. The assembly 100 is portable and mobile. The assembly 100 features a resource management capability that facilitates the monitoring of onboard medical equipment and medical supplies loaded onto assembly 100. In one form, assembly 100 includes a sensor, module, or other suitable device that emits a signal with location data indicating a location of a particular assembly 100. Such a location indicator can be housed or deployed at any part of assembly 100. The signal module transmits a unique signal (i.e., different from similar assemblies that may emit a different signal) to a receiver in communication with a computing device that receives the signal and is capable of pin-pointing the location of the assembly sending the unique signal within a space (e.g., within a particular floor in a hospital building).

A computing device capable of receiving a signal emitted from the assembly to provide the assembly location refers to a device with a processor, memory, network interface, and a storage device. Computing devices are capable of executing instructions. The term computing device includes, but is not limited to, a personal computer, server computers, computing tablets, set-top boxes, video game systems, personal video recorders, telephones, cellular, telephones, digital telephones, personal digital assistants (PDAs), portable computers, notebook computers, and laptop computers. Computing devices may run an operating system, including, for example, variations of the Linux, Unix, MS-DOS, Microsoft Windows, Palm OS, Symbian OS, and Apple Mac OS X operating systems. Computing devices also include communications software that allows for communication over network. Depending on the electronic device, the communications software may provide support for communications using one or more of the following communications protocols or standards: the User Datagram Protocol (UDP), the Transmission Control Protocol (TCP), the Internet Protocol (IP), and the Hypertext Transport Protocol (HTTP); one or more lower-level communications standards or protocols such as, for example, the 10 and/or 40 Gigabit Ethernet standards, the Fiber Channel standards, one or more varieties of the IEEE 802 Ethernet standards, Asynchronous Transfer Mode (ATM), X.25. Integrated Services Digital Network (ISDN), token ring, frame relay, Point to Point Protocol (PPP), Fiber Distributed Data Interface (FDDI); and other protocols. Electronic devices may include a network interface card, network chip, or network chipset that allows for communication over network. Computing devices communicating with one another, in some exemplary embodiments, are interconnected to the Internet through many interfaces, including a network, such as a local area network (LAN) or a wide area network (WAN), dial-in-communications, cable modems, and special high-speed ISDN lines.

With continued reference to FIGS. 1 and 2, the assembly 100, in its upright operational orientation, generally includes a front side 102, a rear side 104, a respective right and left side 106*a,b*, and a respective upper and lower end 108*a,b*. The assembly 100 generally includes a first subassembly or lower portion generally illustrated at 110 and disposed at a lower or bottom space of the upright assembly 100, a second subassembly or intermediate portion generally illustrated at 112 and disposed at a mid-level or intermediate space of the upright assembly 100, and a third subassembly or upper portion generally illustrated at 114 and disposed at an upper or top space of the upright assembly 100. The intermediate portion 112 is generally interposed between the lower portion 110 and upper portion 114.

The assembly 100 includes a chassis, frame or main support structure generally illustrated at 120, which is configured to provide assembly 100 with an erect, upright, stabilized, standing structure. The frame 120 facilitates the support and integration of the lower portion 110, intermediate portion 112, and upper portion 114 of assembly 100 into a single integrated and interconnected unit. The frame 120 includes a wheeled base or deck subassembly generally illustrated at 130, a main or central hub or carrier subassembly generally illustrated at 126, and a support post arrangement generally illustrated at 128. In one form, the support post arrangement 128 includes a pair of fixed, parallel, elongate, vertically-oriented, spaced-apart first support pole 122 and second support pole 124 each extending from and mounted at a lower end to the wheeled base subassembly 130 and mounted at an upper end to main hub carrier subassembly 126. Although the support post arrangement 128 is shown with a pair of support poles or posts 122, 124, this depiction is illustrative and should not be considered in limitation of the present invention, as any number of suitable support-type poles or columns can be used. The pair of support poles 122, 124 directly support the overlying hub subassembly 126 and its payload. The pair of support poles 122, 124 are adapted to provide and otherwise define the vertical spacing between lower portion 110 and intermediate portion 112 of assembly 100. The wheeled base subassembly 130 is adapted to support the intermediate portion 112 and upper portion 114 of assembly 100. The wheeled base subassembly 130 forms part of the lower-level, first subassembly 110. The main hub carrier subassembly 126 forms part of the mid-level, second subassembly 112. Although the support of main hub carrier subassembly 126 above wheeled base subassembly 130 is implemented with a multi-post arrangement, any other suitable support structure can be used. In particular, although frame 120 utilizes a multi-post structure in the form of support post arrangement 128 to provide the support of intermediate portion 112 relative to lower portion 110, any type of suitable support structure well known to those skilled in the art can be used.

Figure 7:
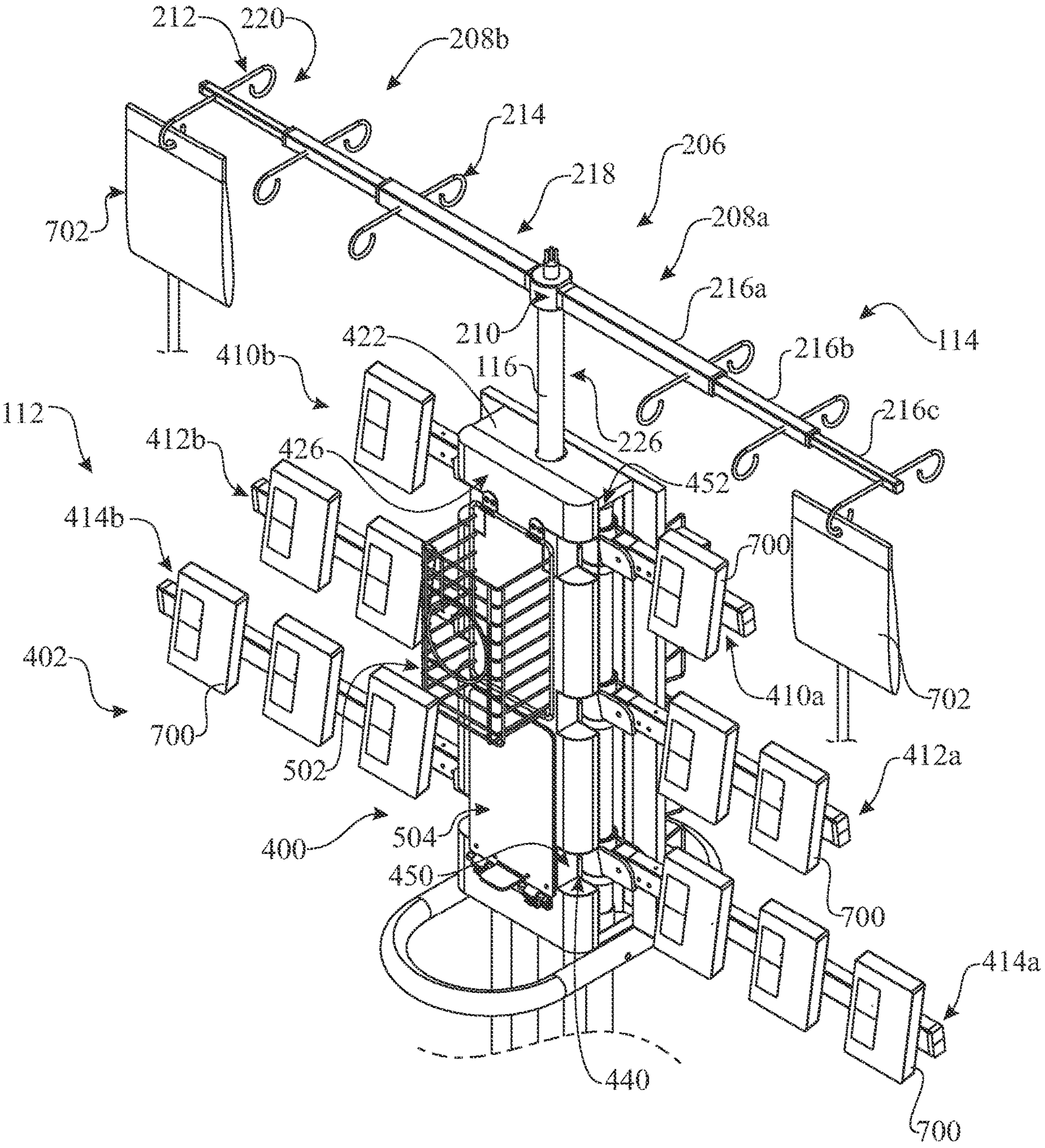
FIG. 7 presents an enlarged, partial, front, upper, right-side isometric view of the intravenous pole assembly illustrated in FIG. 1, more particularly showing the upper portion of the assembly loaded with medical supplies.

Referring to FIGS. 1 and 2, with reference to FIG. 7, the upper portion or upper-level third subassembly 114 of assembly 100 is configured at least in part as a variable-sized, T-shaped, mast-and-boom, rack combination including a height-adjustable feature in the vertical dimension, and a length-adjustable feature in the transverse or horizontal dimension. In one form, the upper-level third subassembly 114 includes, in combination, a length-adjustable, mast-like, vertically-extending, elongate, height-setting and height-variable central pole 116; a length-adjustable, boom-like, horizontally-extending, transverse, hanging-capable, cross-bar rack device 206; and, a rotatable, sleeve-like, bar-supporting, connection hub device 210 configured to rotatably mount the transverse cross-bar rack device 206 to central pole 116. The combination of length-adjustable vertical pole 116 and the length-adjustable horizontal cross-bar rack device 206 has a generally T-shaped configuration (i.e., the vertical pole 116 refers to the stem and the horizontal bar device 206 refers to the arm of the uppercase letter "T").

The upper-level third subassembly 114 further includes a set 212 of individual spaced-apart hook devices 214 carried by the transverse cross-bar rack device 206 along its length. Each hook device 214 is double-sided or double-hooked, enabling it to carry and support containers on both sides of the transverse hanging bar rack device 206. The cross-bar rack device 206 is capable of hanging and otherwise supporting a number of infusion bags 702 (and associated conveyance tubing) via hook devices 214. For example, in the exemplary implementation shown in the figures, the horizontal cross-bar rack device 206 includes a set 212 of six double-sided hook devices 214, enabling a total capacity of twelve infusion bags 702 to be hung. The height-variable vertical pole 116 includes an upper end 226 receiving connection hub device 210 mounted thereon, and a lower end 228 mounted to the lower portion 110 of assembly 100. In one form, the height-variable vertical pole 116 is centrally interposed between the pair of support poles 122, 124 of frame 120 at its lower end 228. The main hub subassembly 126 of second subassembly 112 is appropriately configured to receive central pole 116, which extends through main hub subassembly 126. The main hub subassembly 126 helps position, locate, and support central pole 116 and maintain its vertical orientation.

The height-variable vertical pole 116 is configured as a vertically-oriented telescoping device enabling a user to adjust the height of vertical pole 116, which effectively changes the vertical clearance or separation relative to the underlying central hub subassembly 126. In doing so, the height adjustment also varies and otherwise changes the height or elevation of the upper horizontal cross-bar rack device 206, which is mounted transversally or orthogonally to vertical pole 116. Any conventional means well known to those skilled in the art can be used to adjust the telescoping feature of vertical pole 116 and selectively raise or lower it. For example, vertical pole 116 can be equipped with a lever-type clamping handle generally illustrated at 118 to loosen or tighten the coupling of the telescoping sections of vertical pole 116. The user, for example, can appropriately maneuver or rotate the handle 118 in one direction to release the telescoping sections from their firm mutual engagement, displace the telescoping sections accordingly to enact the desired height adjustment, then rotate the handle 118 in another direction to clamp the telescoping sections together to secure and maintain the new vertical extension of vertical pole 116. The telescoping feature of vertical pole 116 can include any number of individual telescoped arms or sections.

The length-adjustable, transverse, cross-bar rack device 206 is configured in one form as a bilateral telescoping assembly including, in combination, an identical right side and a left side telescoping device 208*a,b*, respectively. Each one of the telescoping devices 208*a,b* has a multi-arm configuration including, for example, a set of telescoping arms 216*a,b,c* each carrying a respective hook device 214. Each multi-armed telescoping device 208*a,b* is independently adjustable. For example, depending on need, the right side telescoping device 208*a* can be fully extended and the left side telescoping device 208*b* partially extended, or vice-versa. Generally, the telescoping devices 208*a,b* can each be deployed in any combination of full extension, partial extension, or no extension. Each telescoping device 208*a,b* is connected at a proximal end 218 to the bar-supporting upper hub 210. Each telescoping device 208*a,b* also includes a distal free end 220. Each telescoping device 208*a,b* extends in a generally orthogonal relationship from vertical pole 116.

The bar-supporting, upper hub device 210 is configured to carry and support each one of the right side and left side telescoping devices 208*a,b* of the length-adjustable, transverse cross-bar rack device 206. In particular, each one of the telescoping devices 208*a,b* is mounted at its proximal end 218 to the bar-supporting hub device 210 so that each telescoping device 208*a,b* maintains its horizontal orientation extending away from vertical pole 116. The hub device 210 can be implemented in any conventional means known to those skilled in the art. For example, the bar-supporting hub device 210 can be configured as a collar or sleeve concentrically mounted on vertical pole 116. The hub device 210 can be configured as a fixed, stationary article or a rotary article. In the rotary configuration, the bar-supporting hub device 210 can rotate relative to vertical pole 116. In this manner, the horizontal cross-bar rack device 206 rotates in tandem or unison with any rotation of hub device 210. The individual hook devices 214 carried by the right side and left side telescoping devices 208*a,b* of the transverse cross-bar rack device 206 can be configured in any conventional manner well known to those skilled in the art. For example, each hook device 214 can have a bilateral pigtail-shaped arrangement having a pair of pigtail hook fasteners, one on each side of the respective telescoping device 208*a,b*. The hook device 214 is positioned generally orthogonal to the generally elongate and linear shape of telescoping device 208*a,b*. The hook device 214 is suitable to hold and support a medical-type fluid bag (e.g., infusion bag 702) hanging from its pigtail-shaped hook end. The upper portion 114 of assembly 100, via the arrangement of hook devices 214, can support articles including, but not limited to, fluid solution bags used by an anesthesiologist care team, critical care staff, and other personnel who are involved, for example, in treatment settings including, but not limited to, pre-operative, operative, and post-operative environments.

The movable feature of upper portion 114 of assembly 100 offers several independent degrees of freedom. The upper portion 114 is configured to enable movements along a vertical or longitudinal axis, a horizontal or transverse axis, and an angular or rotational direction. In particular, the vertical height or extension of central vertical pole 116, and so the elevation of the horizontally-extending transverse cross-bar rack device 206, can be varied and/or adjusted (i.e., raised or lowered) by appropriately changing the telescoping relationship between the telescoped sections of central vertical pole 116. This adjustment to the extension of vertical pole 116 effectuates a change or variation in height along the vertical direction. The height-adjustable central vertical pole 116 enables the upper section 114 to be vertically movable relative to the intermediate portion 112 and lower portion 110 of assembly 100, in order to adjust its height and create more or less space to suspend solution bags 702 from the transverse cross-bar rack device 206.

Additionally, the horizontal extension of the transverse cross-bar rack device 206 can be varied and/or adjusted by appropriately changing the telescoping relationship between the set of telescoping arms 216*a,b,c* of the right side and left side telescoping devices 208*a,b*. This adjustment to the extension of transverse cross-bar rack device 206 effectuates a change or variation in length in the horizontal direction. Moreover, the angular orientation of the transverse cross-bar rack device 206 can be varied and/or adjusted by appropriately changing the rotational position of the bar-supporting rotary hub 210. This adjustment to the bar-supporting rotary hub 210 makes a commensurate rotational adjustment to the angular position of the transverse cross-bar rack device 206. All of these adjustments, changes, and variations in position and dimension can be made on an as-needed basis to accommodate the spacing and access requirements of the healthcare setting, such as situating medical supplies at a location deemed more suitable for the attending clinical team and/or patient.

Referring now to FIGS. 1-2 and 5-6, the lower portion or lower-level first subassembly 110 of assembly 100 includes, in combination, the wheeled base subassembly 130 configured at least in part to make assembly 100 mobile and transportable, and an electrical unit or assembly generally illustrated at 236 and configured at least in part to provide a power supply and electrical interfaces to support power and data connections. Shown individually in FIG. 6, the wheeled base subassembly 130 is able to move and station assembly 100 at any location where it is needed, including, but not limited to, an operating room theater, hospital room and hallways, and intensive care unit facility.

Figure 6:
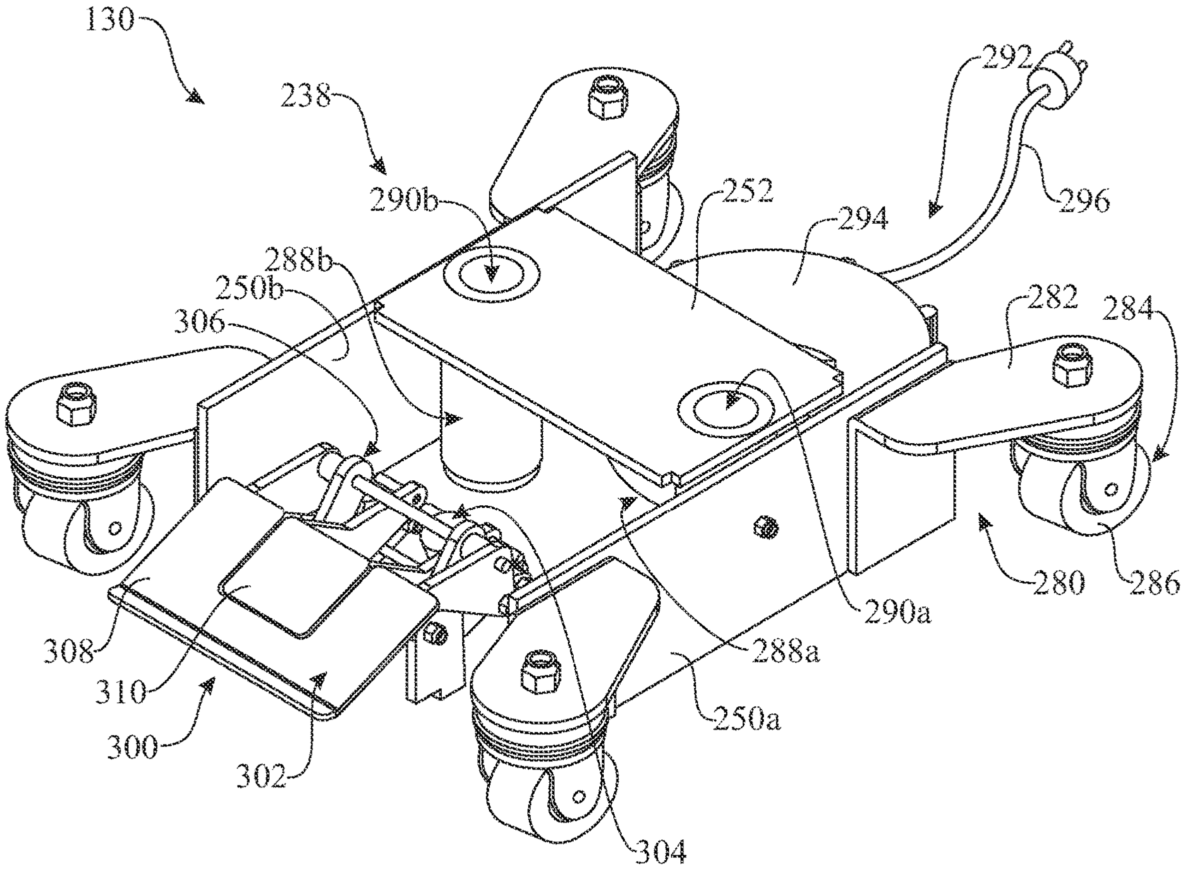
FIG. 6 presents a front, upper, right-side isometric view of a wheeled base used in the intravenous pole assembly illustrated in FIGS. 1 and 5.

Referring specifically to FIG. 6, the wheeled base subassembly 130 includes a chassis or frame generally illustrated at 238 including a pair of vertically-extending, spaced-apart sidewalls 250*a,b* and an upper pole-receiving and pole-supporting plate 252 extending horizontally between the pair of vertical sidewalls 250*a,b*. The chassis 238 has a generally rectangular-shaped configuration and forms a sturdy, robust base structure to support the weight and loading of assembly 100 in a stable, tip-resistant configuration. The wheeled base subassembly 130 is equipped at each one of its four corners with a swiveling wheel assembly 280 including, in combination, a chassis-coupling bracket 282 and a swivel-type caster wheel arrangement 284 including a swivel wheel 286. The swiveling wheel assembly 280 is configured to provide wheel 286 with multi-directional and/or omnidirectional movement, i.e., wheel 286 can pivot or swivel in a full revolution or 360 degrees of freedom. The chassis-coupling bracket 282, in one form, extends in a generally diagonal direction from a respective corner of the base chassis 238, so that the set of caster wheel arrangements 284 are disposed in a sufficient spaced-apart relationship to chassis 238 to enhance the stability of the wheeled base subassembly 130. The wheeled feature of base subassembly 130 provides assembly 100 with a sharp turning radius, enabling it to maneuver easily within the limited space of some application environments, such as a critical care unit already staffed with multiple pieces of equipment and personnel.

The wheeled base subassembly 130 further includes a pair of pole-receiving, bore-shaped tubular elements 288*a,b* extending downwards from the underside of upper horizontal plate 252 of chassis 238. The tubular elements 288*a,b* respectively, include an open upper or top end 290*a,b* and a terminal closed lower or bottom end. The tubular elements 288*a,b* are sufficiently sized, shaped and dimensioned so that their lower end terminus maintains an adequate spaced-apart relationship to the underlying ground surface that wheeled base subassembly 130 engages. During assembly, the pair of first support pole 122 and second support pole 124 are each received and inserted within the pair of tubular elements 288*a,b*, respectively, via the open top ends 290*a,b*. The poles 122, 124 slide through their respective tubular elements 288*a,b* until they contact the closed bottom ends, where the poles 122, 124 remain in a fixed, seated position. The tubular elements 288*a,b* are appropriately sized, shaped and dimensioned to ensure that support poles 122, 124 can slidably displace through them. The insertion of support poles 122, 124 in tubular elements 288*a,b* provides a secure mounting of poles 122, 124.

The wheeled base subassembly 130 further includes a foot-actuated, parking-type brake system generally illustrated at 300 configured to selectively and releasably apply a braking action to stop and/or prevent movement of assembly 100 and secure it in place. The brake system 300 would be activated, for example, when assembly 100 is stationed at its operational location (e.g., surgical room). The brake system 300 includes, in combination, a foot-activated brake pedal device 302, a movable rubber stem floor stop 304, and a mechanism generally illustrated at 306 configured to control the movement of rubber stem floor stop 304 in response to user actuation of brake pedal device 302. The mechanism 306 controls the up and down movement of rubber stem floor stop 304 in response to the actuation of brake pedal device 302. In particular, the floor stop 304 is selectively movable between a released, non-braking position in which floor stop 304 is spaced-apart from the floor surface in a non-contact relationship to permit mobility of assembly 100, and a locked, braking position in which floor stop 304 is displaced into frictional, contacting engagement with the ground or floor surface to resist and/or prevent movement of assembly 100. The bottom, ground-contacting surface of floor stop 304 is preferably sized, shaped and dimensioned to provide optimal brake-inducing frictional engagement with the travel surface it contacts. The mechanism 306, in one form, employs a lever arrangement to translate the activation of pedal device 302 into an appropriate vertical displacement of floor stop 304. The floor stop 304 is normally in an elevated position relative to the ground, during non-activation of brake pedal 302. For ease of assembly, maintenance and compactness, the braking element is preferably provided in the form of a single such floor stop 304, which is suitably sized, shaped and dimensioned for this all-in-one braking applicator. However, it should be apparent to those skilled in the art that more than one braking element 304 can be used to simultaneously, frictionally engage the driving surface at multiple points of contact.

The brake pedal device 302 includes a locking pedal 308 and a release pedal 310 to facilitate the braking and non-braking modes of wheeled base subassembly 130, respectively. The locking pedal 308 and release pedal 310 are independently activated. During a braking action, the user depresses the locking pedal 308, which activates and cooperates with mechanism 306 to move and dispose the rubber stem floor stop 304 into frictional engagement with the ground, which arrests and otherwise impedes further movement of assembly 100. During the braking period, the locking pedal 308 remains depressed and pivoted relative to release pedal 310, so that release pedal 310 adopts an elevated position relative to locking pedal 308, making it easy to access and accurately target. During a release action, the user depresses the release pedal 310, which activates and cooperates with mechanism 306 to release floor stop 304 from its frictional engagement with the ground and to place the released floor stop 304 in an elevated position relative to the ground, rendering assembly 100 mobile again. At the same time, the locking pedal 308 returns to its original, pre-locking position.

Figure 5:
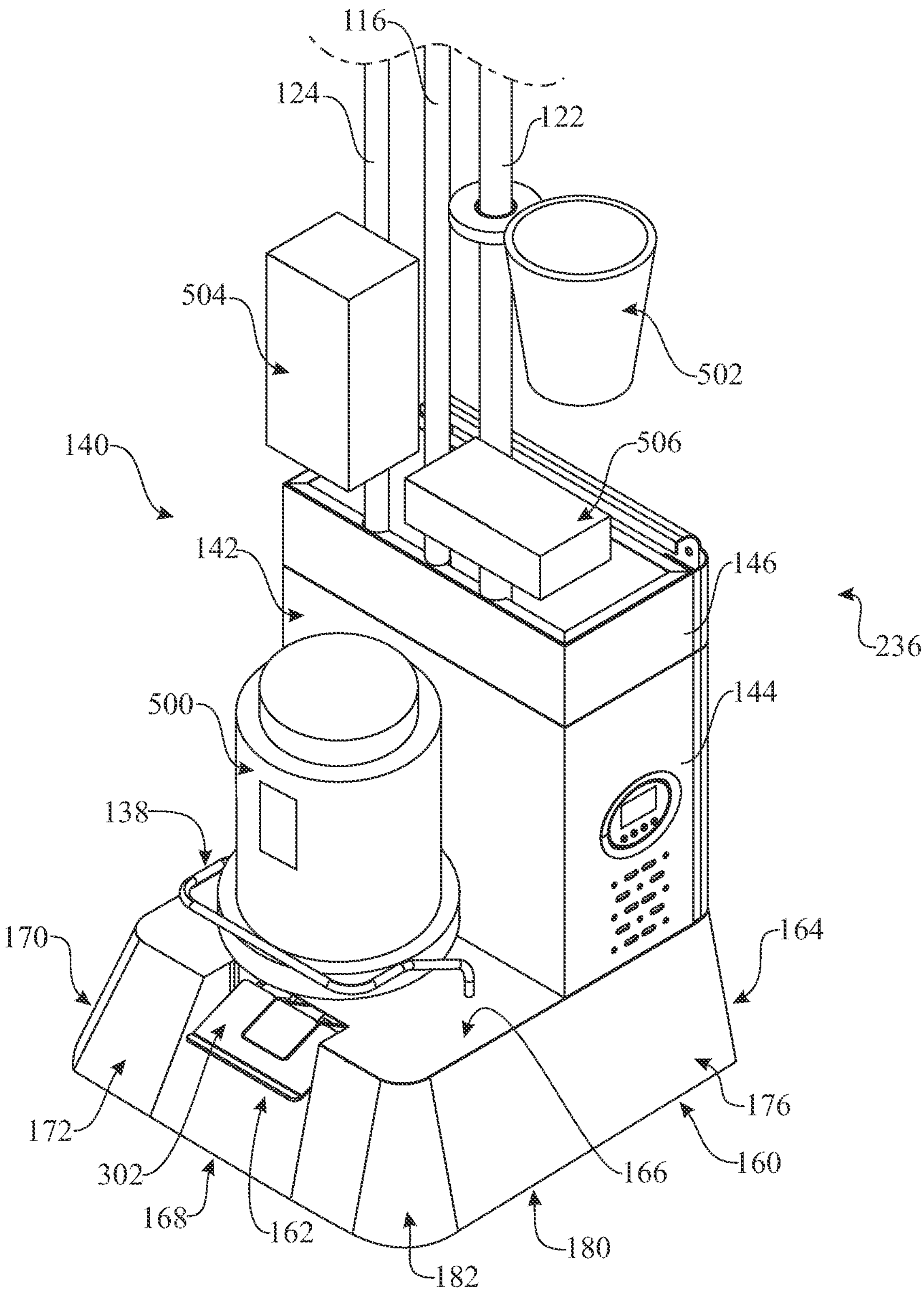
FIG. 5 presents a partial, front, upper, right-side isometric view of the intravenous pole assembly illustrated in FIG. 1, more particularly showing the components for the lower portion of the assembly.

Referring still to FIGS. 1-2 and 5, the lower-level first subassembly 110 includes a skirt-shaped barrier or protective covering in the form of a shield, shell or cover 160 configured to cover the wheeled base subassembly 130 and to provide a front opening generally illustrated at 162 for access to brake pedal 302. The cover 160 includes a generally rectangular-shaped body generally illustrated at 164 having a generally planar upper or top side 166 defining a mounting platform, an open bottom generally illustrated at 168 configured to make space for the wheeled base subassembly 130, and a lateral, multi-sided, foot-type structure generally illustrated at 170 configured to fully, peripherally enclose the wheeled base subassembly 130. In one form, the lateral structure 170 is configured as a sidewall arrangement, which includes a set of peripheral sidewalls each extending and/or depending generally downward and outward from upper side 166 at a respective edge thereof. In its sidewall configuration, the lateral structure 170 includes a front side 172, a rear side 174, a right side 176, and a left side 178. In order to establish a footprint compatible with the geometry of the enclosed wheeled base subassembly 130, each side of the lateral structure 170 preferably transitions to an adjoining side using a generally rounded or curved corner 182 to accommodate an appropriately-sized fit or capture of a respective caster wheel arrangement 284 and its associated chassis-coupling bracket 282 (FIG. 6). The lateral structure 170 defines a bottom edge periphery generally illustrated at 180. Each sidewall of lateral structure 170 forms a ramplike, sloping surface extending downward and outward from the top side 166 to the bottom edge periphery 180.

The upper or top side 166 of base cover 160 is adapted with suitable openings (not shown) to receive the first support pole 122 and second support pole 124 so that poles 122, 124 can access and make passage into the pair of pole-receiving tubular elements 288*a,b* of chassis 238 of wheeled base subassembly 130. The cover 160 extends completely over and contains the wheeled base subassembly 130 shown in FIG. 6. A suitable means can be provided to attach cover 160 to chassis 238 of subassembly 130 to fix its location.

A retention railing 138 is disposed at upper side 166 of cover 160. The retention railing 138 has a generally U-shaped configuration, in which its free ends have a bent or angled form that extend from upper side 166 of cover 160 so that its generally central body portion defines a forward guard rail elevated from upper side 166. The retention railing 138 defines an interior holding space configured to receive, hold, and retain medical equipment disposed on upper side 166 of cover 160 at a forward, front location. The lower edge 180 of base cover 160 is adapted to be sufficiently close to the ground to prevent items and other potential entanglements lying on the floor from going underneath it and interfering with wheels 286 (e.g., floor cables), yet sufficiently far away from the ground to allow assembly 100 to move freely via its wheeled maneuvering and transport.

Referring briefly to FIG. 5, the lower portion or lower-level first subassembly 110 of assembly 100 is able to securely receive, hold and otherwise carry a variety of pieces of medical equipment and supplies during operational loading. Generally, assembly 100 provides a centralized location for housing various medical devices, accessories and supplies. For example, an air blower device generally illustrated at 600 can be housed, retained and carried by assembly 100 in the interior holding space defined by retention railing 138 disposed at the upper side 166 of base cover 160. The blower device 600 can provide temperature management to the ambient environment. A cup or blood reservoir generally illustrated at 602 can be releasably attached to one of the support poles 122, 124. A massive transfusion set generally illustrated at 604 (including pump and blood reservoir) can be securely and removably mounted to one of the support poles 122, 124. A fluid warmer device generally illustrated at 606 can be securely and removably mounted to one of the support poles 122, 124. The pole-mounted medical equipment 602, 604, 606 is adequately positioned along poles 122, 124 to provide easy access by medical personnel. The air blower device 600 is suitably positioned at a low enough location on the upper side 166 of base cover 160 to provide an adequate airflow near the ground surface. The medical equipment and/or device can be mounted to the poles 122, 124 using any conventional means well known to those skilled in the art. For example, a releasable, adjustable, press-fit clamp can be used to mount the devices on poles 122, 124, allowing height and rotation adjustment. In particular, depending on need and available space, the mounted medical devices can be placed at any suitable point along the exposed vertical section of poles 122, 124 and oriented at any rotational position to enhance access and usability.

Referring again to FIGS. 1 and 2, the electrical subassembly 236 of the lower portion or lower-level first subassembly 110 of assembly 100 includes a rechargeable, uninterruptible power supply (UPS) unit generally illustrated at 140. The UPS unit 140 includes, in combination, a housing or enclosure 142 and a UPS device housed in enclosure 142. The housing 142 can be divided into a lower compartment generally illustrated at 144 housing the UPS device, and an upper compartment generally illustrated at 146 housing a retractable cable reel (not shown). The UPS unit 140 provides backup power to all medical electronics loaded onto assembly 100, in the event that external power is unavailable or interrupted. The location of UPS unit 140 on the wheeled base subassembly 130 of lower portion 110 can be made in any convenient manner. In one form, for example, the UPS unit 140 is located at a rear section of the upper side 166 of base cover 160, while the railing 138 is located at a forward section.

The electrical subassembly 236 further includes an electrical grid or hub housed in UPS unit 140 and configured to distribute electricity from multiple energy sources to multiple devices loaded onto assembly 100. The assembly 100 can be powered by connection to an external power source or by utilization of the onboard, resident power source (i.e., UPS device housed in UPS unit 140). For example, referring to FIG. 6, the wheeled base subassembly 130 can be adapted to carry a retractable cable reel assembly 292 having a coiled reel body 294 configured to feed out a power cable having a bottom-exiting power input plug 296. The retractable cable reel 292 can be carried, for example, at the rear end of chassis 238 of subassembly 130. The bottom-exiting power input plug 296 can be routed through an exit aperture formed in the rear side 174 of base cover 160 (FIG. 2) and plugged into an outlet of the external environment, e.g., a wall outlet in a hospital room. Another retractable cable reel housed in the upper compartment 146 of housing 142 of UPS unit 140 includes a cable-connected electrical input plug 224 that is routed vertically through the hollow interior of the height-variable central vertical pole 116 until it exits from an opening at the top of pole 116 (FIG. 2). This top-exiting power input plug 224 can be plugged into an outlet of the external environment, e.g., a ceiling outlet in a hospital room. The electrical subassembly 236 further includes an electrical panel generally illustrated at 240 (FIG. 2) having a set of communication and power interfaces, such as electrical outlets and USB ports. The electrical panel 240 enables external cable connections to be made to electrical subassembly 236, in order to provide power and data communication to assembly 100. For example, the electrical outlets of electrical panel 240 enable a user to make a connection from an external power supply (e.g., local power gird) to assembly 100 to supply power. The USB ports of electrical panel 240 enable connection to a wide variety of peripheral devices for charging purposes, e.g., a mobile device, portable computer device, and a laptop. Alternately, the electrical outlets of electrical panel 240 can be used to provide power from the UPS device to other sections of assembly 100, in which case a user needs to supply a cable to make the connection. The electrical outlets of electrical panel 240 provide an additional and/or alternate means of providing power to assembly 100, in addition to the UPS device housed in UPS unit 140 and the cable hook-ups to external power sources via the bottom-exiting power input plug 294 and top-exiting power input plug 224. The UPS unit 140 may be further equipped with other options, including, but not limited to, ventilation ports 242 formed in housing 142 to maintain proper temperature management of the enclosed electrical equipment, a UPS device status display 244, fuses, and pilot lights.

Referring now to FIGS. 1-4 and 7, the intermediate or mid-level portion 112 of assembly 100 is configured at least in part as a multi-arm, power-feeding, rack apparatus to hold, support and otherwise carry various medical supplies and devices, including, but not limited to, infusion pumps. The mid-level second subassembly or middle portion 112 of assembly 100 includes the main hub or carrier subassembly 126. The carrier subassembly 126 includes a hub portion generally illustrated at 400 and a rack-forming arm subassembly generally illustrated at 402 and carried by hub portion 400. The rack-forming arm subassembly 402 includes a pair of upper-level fixed-length arms 410*a,b*, a pair of mid-level or intermediate fixed-length arms 412*a,b*, and a pair of lower-level fixed-length arms 414*a,b*. The arms of arm subassembly 402 are configured in a tree-like, multi-branch arrangement. Each arm of the arm subassembly 402 is configured, in one form, as a power-capable infusion pump holder, i.e., each arm is equipped to provide power to the mounted or loaded infusion pump. Additionally, each arm of the arm subassembly 402 is capable of rotational or pivoting motion about a vertical axis to displace the arms in a transverse or horizontal plane (FIG. 4), and is further capable of rotational or pivoting motion about a horizontal axis (anterior-to-posterior direction) to displace the arms in the frontal or vertical plane so as to facilitate the transition of the arm between a deployed, extended orientation (FIG. 3A) and a stowed, retracted orientation (FIG. 3B). Unless otherwise noted, each arm of the rack-forming arm subassembly 402 is identically constructed and has the same functionality, so a reference to one applies equally to the other. Although a set of three pairs of arms is shown, the depiction of six horizontal retractable arms is merely illustrative and should not be considered in limitation as it should be apparent to those skilled in the art that any number of arms can be employed.

The hub portion 400 of main carrier subassembly 126 includes a generally rectangular-shaped body generally illustrated at 420 having a top side 422, a bottom side 424, a front side 426, a rear side 428, and a pair of right and left sides 430*a,b*. Each corresponding pair of arms of arm subassembly 402 are generally disposed at opposite sides of the body 420 of hub portion 400. For example, the pair of upper arms 410*a,b*, are generally disposed at the opposite right and left sides 430*a,b*, respectively, of body 420; the pair of intermediate arms 412*a,b* are disposed at the opposite right and left sides 430*a,b*, respectively, of body 420; and, the pair of lower arms 414*a,b* are disposed at the opposite right and left sides 430*a,b*, respectively, of body 420. The arm subassembly 402 is carried by the main carrier subassembly 126 at hub portion 400. The pairs of arms 410*a,b*, 412*a,b*, and 414*a,b* are disposed in a spaced-apart relationship along a vertical or longitudinal dimension of hub portion 400. Additionally, in one form, the arm lengths may be uniform or variable. For example, as depicted, the arm lengths from one level to the next may get progressively shorter or longer, i.e., the lower-level arms 414*a,b* are the longest (and same or equal length), the mid-level arms 412*a,b* are the next longest (and equal length), and the upper arms 410*a,b* are the shortest (and equal length). The body 420 of hub portion 400 can be adapted to allow the central vertical pole 116 to extend through its interior space, in which pole 116 passes through apertures or pole-receiving holes formed in the bottom side 424 and top side 422. The upper or distal ends of the pair of support posts 122, 124 are attached to the bottom side 424 of hub body 420.

The illustrative right-side lower arm 414*a* is mounted to the hub portion 400 of main carrier subassembly 126 by a multi-axial pivot joint generally illustrated at 440. For example, in one form, the multi-axial pivot joint 440 is implemented as a biaxial ball-and-socket joint, offering independent rotation about two reference axes and corresponding movement (displacement) in two planes. However, this implementation is merely illustrative and should not be considered in limitation of the present invention, as it should be apparent to those skilled in the art that any other suitable multi-axial pivot joint can be used. For example, the multi-axial pivot joint 440 can be configured as an articulating, double-bracket, linkage structure having two shafts defining two different axes of rotation. In this configuration, each shaft-and-bracket combination cooperates with the other shaft-and-bracket combination to allow a workpiece attached to it (i.e., arm 414*a*) to rotate about a first axis defined by a first one of the shafts and to rotate about a second axis defined by the second one of the shafts. In another multi-axis pivot configuration, the proximal end 442 of illustrative arm 414*a* is rotationally or pivotably coupled to a pivot axis extending between the sides of a U-shaped bracket, defining a horizontal axis of rotation for arm 414*a* enabling it to pivot and displace through a vertical plane. The opposite end of this U-shaped pivot bracket is fixedly coupled to a bracket-type sleeve rotatably mounted to a vertical shaft, defining a vertical axis of rotation for arm 414*a* enabling it to pivot and displace through a transverse plane. This vertical shaft defines the vertical axis of rotation for all of the same-sided arms 410*a*, 412*a*, and 414*a*. The multi-axis pivot joint 440 is preferably configured to ensure that arm 414*a*, when deployed, maintains a horizontal orientation (i.e., arm 414*a* cannot pivot below the horizontal plane). This can be implemented, for example, by resting or seating a portion of the proximal end 442 of illustrative arm 414*a* in the saddle of the U-shaped pivot bracket.

Figure 3A:
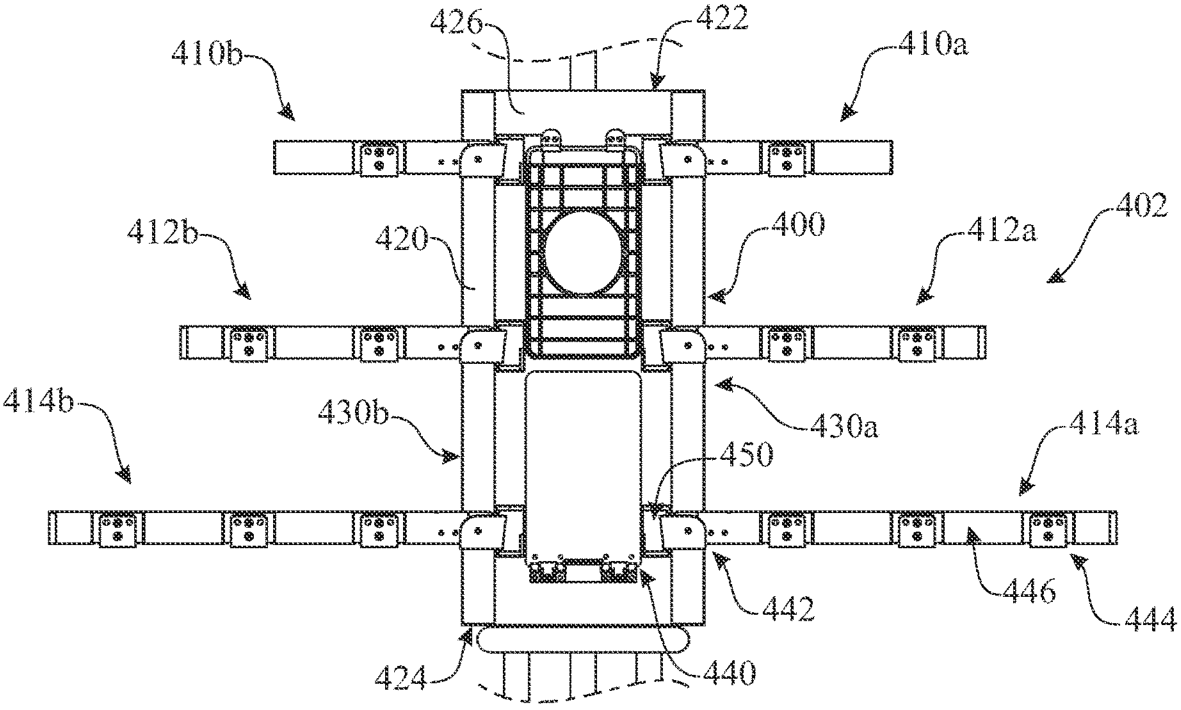
FIGS. 3A and 3B present partial front elevation views of the intravenous pole assembly illustrated in FIG. 1, more particularly showing the arrangement of horizontal support arms in their extended and retracted positions, respectively.
Figure 4:
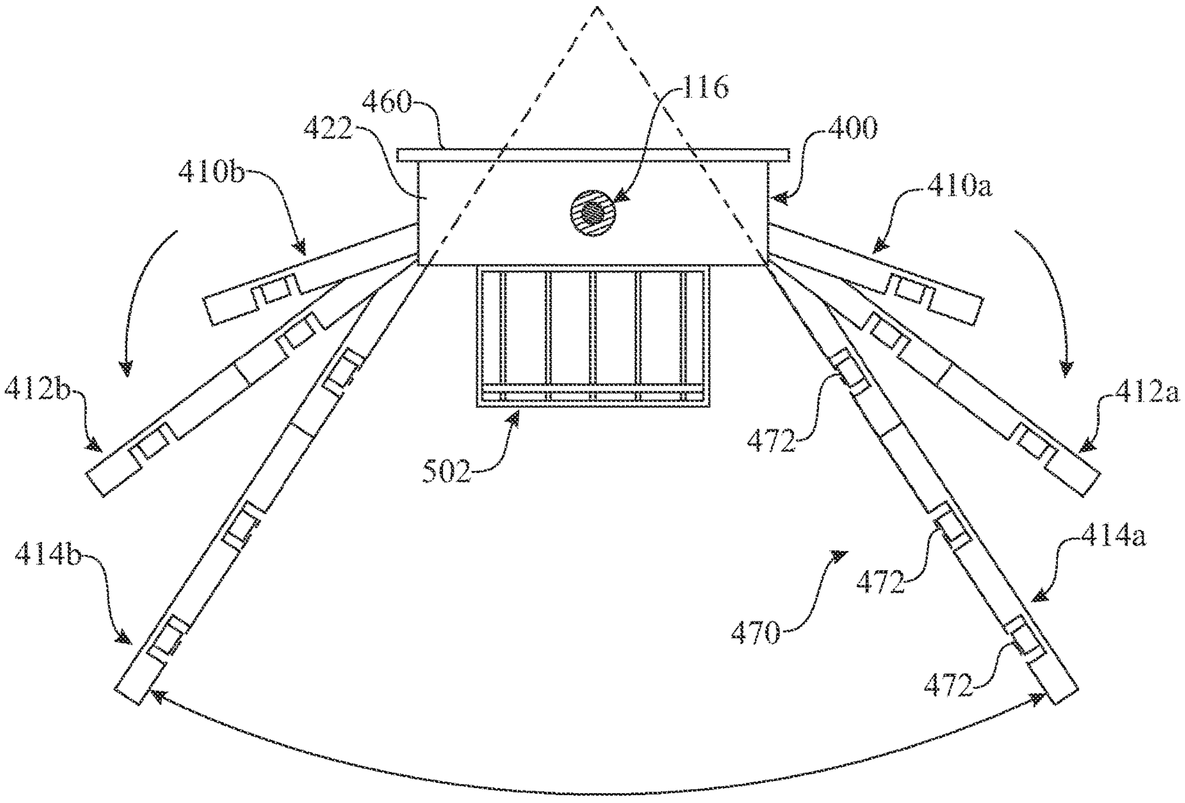
FIG. 4 presents a partial upper plan view of the intravenous pole assembly illustrated in FIGS. 1 and 3A-B, more particularly showing how the deployed support arms can be pivoted forward at selected angular orientations.

The illustrative right-side lower arm 414*a* has proximal end 442 and distal end 444 (FIG. 3A). The arm 414*a* includes a generally elongate body 446 extending between the proximal end 442 and the distal end 444. The lower arm 414*a* is coupled at its proximal end 442 to pivot joint 440 in a pivot-ready, pivot-capable, articulating relationship. In this manner, each arm of arm subassembly 402 forms an articulating relationship to the hub portion 400 of main carrier subassembly 126. The articulation of the arms is configured to enable the same-side arms (i.e., the set of left-side arms 410*b*, 412*b*, and 414*b* and the set of right-side arms 410*a*, 412*a*, and 414*a*) to pivot or rotate about a respective common vertical axis and move through a distinct transverse or horizontal plane. Each corresponding pair of right-side and left-side arms (e.g., right-side and left-side arms 410*a,b*) preferably rotates through its own common transverse plane. Thus, in the configuration shown, the three sets of corresponding arm pairs 410*a,b*, 412*a,b*, and 414*a,b* are capable of deployment and transverse rotation through three individual horizontal planes. In their deployed configuration, as shown in FIGS. 1-2, the arms of arm subassembly 402 extend away from hub portion 400 of main carrier subassembly 126. As shown in FIG. 4, any one of the arms can be independently pivoted or rotated about the vertical axis of its respective pivot joint to another angular displacement. For example, the right-side arms can be pivoted into a staggered relationship (i.e., different angular displacements), so that the lower-level right-side arm 414*a* is rotated the most, the upper-level right-side arm 410*a* is rotated the least, and the mid-level right-side arm 412*a* is rotated intermediate the other two. The same or similar relationship can be produced for the left-side arms 410*b*, 412*b*, and 414*b*. The pivoting relationship shown in FIG. 4 is for illustrative purposes only and merely exemplary, as it should be apparent to those skilled in the art that any arm can be displaced (rotated) through its respective transverse plane of movement independently of the other arms. The forward rotation of the arms of arm subassembly 402 may be beneficial to bring the items loaded onto the arms closer to the personnel who need to access them (e.g., FIG. 7). In one form, the arms of arm subassembly 402 have a generally ninety degree range of motion through the respective transverse plane. During deployment, the illustrative right-side lower arm 414*a* can pivot, for example, from an orientation generally orthogonal to the right side 430*a* of body 420 of hub portion 400 of carrier subassembly 126 (e.g., FIGS. 1 and 2), to an orientation generally orthogonal to the front side 426.

The hub portion 400 of carrier subassembly 126 is suitably adapted to accommodate the movement or pivoting rotation of each arm of the rack-forming arm subassembly 402 through its respective transverse plane. For example, in reference to the illustrative right-side lower arm 414*a*, a cut-out or recessed arm-guiding slot generally illustrated at 450 is formed in the body 420 of hub portion 400 and cooperates with illustrative arm 414*a* to facilitate its range of motion about a vertical axis through the horizontal or transverse plane. A similar such cut-out 450 is associated with each other arm of the rack-forming arm subassembly 402. The cut-out or arm-guiding slot 450 generally extends between a lateral side of body 420 (i.e., right side 430*a*) and the front side 426 of body 420. The pivot joint 440, in one form, is located within the cut-out 450. This side-to-front extension of cut-out 450 enables a range of motion for arm 414*a* that extends continuously between a first orientation (i.e., extending laterally or in the rightward direction generally orthogonal to right side 430*a*) and a second orientation (i.e., extending in the frontward direction generally orthogonal to front side 426). The cut-out 450 is suitably formed to cooperate with the configuration of arm 414*a* to enable the transverse plane movement of arm 414*a*. For example, the pivoting transition of lower arm 414*a* from its lateral position to its anterior position entails an angular displacement that may require cut-out 450 to have a curvature extending from the right side 430*a* to the front side 426 through the adjoining edge. One feature of using a cut-out 450 to guide the movement of arm 414*a* is that the accompanying pivot joint 440 remains largely hidden-away or out of view in the recess-type configuration of cut-out 450.

Referring still to FIGS. 1-4 and 7, with specific reference to FIG. 3A, the illustrative arm 414*a*, as stated previously, is capable of rotating or pivoting about a horizontal axis through a vertical plane. This movement is useful to transition the arm 414*a* between its generally horizontally-extending deployed position (FIG. 3A) and its generally vertically-extending stored or retracted position (FIG. 3B). For this purpose, the hub portion 400 of carrier subassembly 126 is suitably adapted to accommodate the pivoting rotation of each arm into a generally vertical position to facilitate retraction and stowage. In one form, for example, in reference to the illustrative right-side lower arm 414*a*, a generally vertically-extending, arm-receiving slot, channel or recess generally illustrated at 452 is formed in the body 420 of hub portion 400 at right side 430*a* to receive lower arm 414*a* as it is pivoted into a generally vertical position (corresponding to a retracted, stowage-ready position). The arm-receiving channel 452 is shared in common by all of the retracted same-side arms (e.g., right-side upper arm 410*a*, right-side intermediate arm 412*a*, and right-side lower arm 414*a*). A similar such arm-receiving slot 452 is formed at left side 430*b* of body 420 to accommodate the retracted placement, seating and stowage of the left-side arms 410*b*, 412*b*, and 414*b*.

Figure 3B:
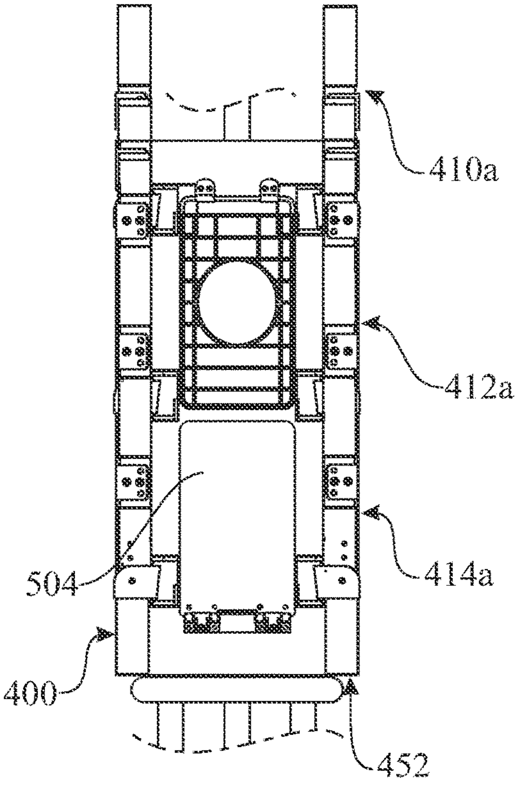

In their originally deployed condition, without any forward angular displacement, the same-side set of arms all generally lie in a common vertical plane generally perpendicular to one of the lateral sides of body 420, e.g., the right-side upper arm 410*a*, right-side intermediate arm 412*a*, and right-side lower arm 414*a* lie in a shared, common vertical plane (FIGS. 1-2). During retraction, the deployed arms are first returned to their most rearward position (FIG. 3A) (i.e., no forward-directed angular displacement) and then the arms are each pivoted upwards into a generally vertical position for collective placement and seating in arm-receiving slot 452 (FIG. 3B). The arm-receiving slot 452 can be sized, shaped and dimensioned to create a recess producing different retraction profiles or folding arrangements of the retracted arms. FIG. 3B depicts one such profile, in which the raised, retracted arms have a generally vertical alignment. In order to present such a streamlined appearance, and allow all the same-sided arms to be pivoted vertically upward through the same vertical plane and yet fold together in general vertical alignment, the vertically-extending arm-receiving slot 452 formed laterally in body 420 is made to extend sufficiently deep into the respective right and left sides 430*a,b* to accommodate the reception and placement of all three same-sided arms in a general vertical orientation. This streamlining feature stows the retracted arms in an arrangement that limits snagging or interference due to arm protrusions, especially during transport. The arms at one side can be deployed and/or retracted in any combination. For example, in a superior arm-hanging option, the right-side upper-level arm 410*a* is deployed (extended horizontally, no angular displacement), while the other two arms 412*a* and 414*a* are retracted. In an inferior option, the lower-level arm 414*a* is deployed while the other two arms 410*a*, 412*a* are retracted. In a median option, the mid-level arm 412*a* is deployed while the other two arms 410*a*, 414*a* are retracted.

Referring still to FIGS. 1 and 2, with reference to FIG. 7, each arm of the rack-forming arm subassembly 402 of the mid-level carrier subassembly 126 is configured to mount and carry a set of medical devices, including, but not limited to, infusion pumps. For example, FIG. 7 depicts an illustrative loading arrangement in which the individual arms of the upper-level 114, mid-level 112 and lower-level 110 each receive one, two, and three infusion pumps 700, respectively, for a total of twelve available pumps 700. Different types of mounting relationships are possible. In a cabled option, in which the mounted infusion pump 700 uses a cabled power hookup, the pump 700 can be releasably mounted to illustrative left-side upper arm 410*b* using an adjustable and re-positionable quick-connect bracket 710 (FIG. 2). A power cable then runs from the bracket-mounted pump 700 to an available socket or electrical outlet in assembly 100.

Alternately, in a cable-free or cable-less application, each arm of the rack-forming arm subassembly 402 is configured as a power rail equipped with a set of cordless power-delivery interfaces. For example, in the illustrative right-side lower-level arm 414*a*, a set 470 of three cordless contact-charging, mounting brackets or charging ports 472 is disposed in a spaced-apart relationship along the length of arm 414*a*. In this cordless option, the infusion pump 700 comes fitted with a compatible bus-type interface or port that mates with the interface or charging port provided by the cordless contact charging bracket 472 installed on arm 414*a*. The releasable mounting of the infusion pump 700 simply entails connecting the interfaces together, e.g., sliding the interface port at the back side of infusion pump 700 onto its dedicated cordless contact charging bracket 472 to form a power-communicating, mounting relationship offering a plug-andplay capability. Assembly 100 provides increased capacity for medical assets. For example, the six horizontal retractable arms offer a capacity for twelve IV infusion pumps, some or all of which may be used on an as-needed basis. If some arms are not loaded, and remain idle, they can be retracted upwards and independently stowed away. In use, the arms can be adjusted to position or move the arms forward closer to the needed work area (e.g., patient) or application. The charging port 472 can have any conventional construction, including, but not limited to, a physical connector that mates with another connector (e.g., a type of plug) to electrically connect two devices.

Referring to FIG. 2, the carrier subassembly 126 of mid-level portion 112 of assembly 100 includes a rear or back-facing, posterior electrical panel generally illustrated at 460 disposed at the rear side 428 of body 420 of hub portion 400 of carrier subassembly 126. The rear electrical panel 460 includes a set 462 of electrical outlets 464 available to provide power to any electronics loaded onto assembly 100. For example, the rear electrical panel 460 can provide power to the array of cabled infusion pumps 700 loaded onto the rack-forming arm subassembly 402. This powering feature is especially useful when the infusion pumps 700 have a cabled arrangement. In the cabled version, the mounted infusion pumps 700 are provided with a power cord connecting them to one of the electrical outlets 464 housed on the rear electrical panel 460. The electrical panel 460 will be configured to provide the number of electrical outlets 464 commensurate at least with the capacity or maximum number of cabled infusion pumps 700 mounted to arm subassembly 402. The rear electrical panel 460 includes a cable organizer or comb generally illustrated at 466 configured to organize any cables extending between the mounted infusion pumps 700 and the electrical outlets 464 of rear electrical panel 460. The cable organizer comb 466 includes multiple individual cord organizing elements 468. The posterior cable organizer 466 provides a means to efficiently and securely the coils of each power cable independently from the other cables.

The upper-level third subassembly or upper portion 114 of assembly 100 can be equipped with various optional features to enhance the user experience and provide additional versatility. An oval-shaped, circular or elliptical, peripheral handle bar 500 can be provided at an appropriate location to facilitate better control for maneuvering assembly 100 during transport and other occasions of mobility. In one form, for example, the drive-type handle bar 500 encircles the set of height-variable vertical pole 116 and first and second fixed support poles 122, 124 at a point below main hub and carrier subassembly 126. The handle bar 500 can be attached to assembly 100 in any conventional manner. The handle bar 500 can be optionally equipped with a loop strap for additional control. An open-top, front mesh auxiliary basket 502 can be disposed at the front side 426 of body 420 of hub portion 400 of carrier subassembly 126. The basket 502 can hold an assortment of loose items (e.g., glove box) and/or secure hardware connected to the patient, such as a cardiac pacemaker. A front foldable tray 504 can be disposed at the front side 426 of body 420 of hub portion 400 of carrier subassembly 126. The tray 504 is pivotably or hingedly mounted to the front side 426. When not in use, tray 504 adopts a retracted or folded-up position in which it lies against front side 426 in a generally parallel and/or abutting relationship. When deployed, tray 504 adopts a pivoted or folded-down position in which it extends horizontally forward from front side 426 in a cantilever-type configuration. The tray 504, for example, provides a working surface for various tasks, such as prepping medications. The deployed tray 504 reveals a set of electrical connections accessible at the front side 426 of body 420 of hub portion 400 of carrier subassembly 126, such as an electrical outlet and USB charger. These tray-adjacent electrical connections facilitate the charging of personal mobile devices and electronics of staff personnel, who can place the recharging devices on deployed tray 504.

Figure 8:
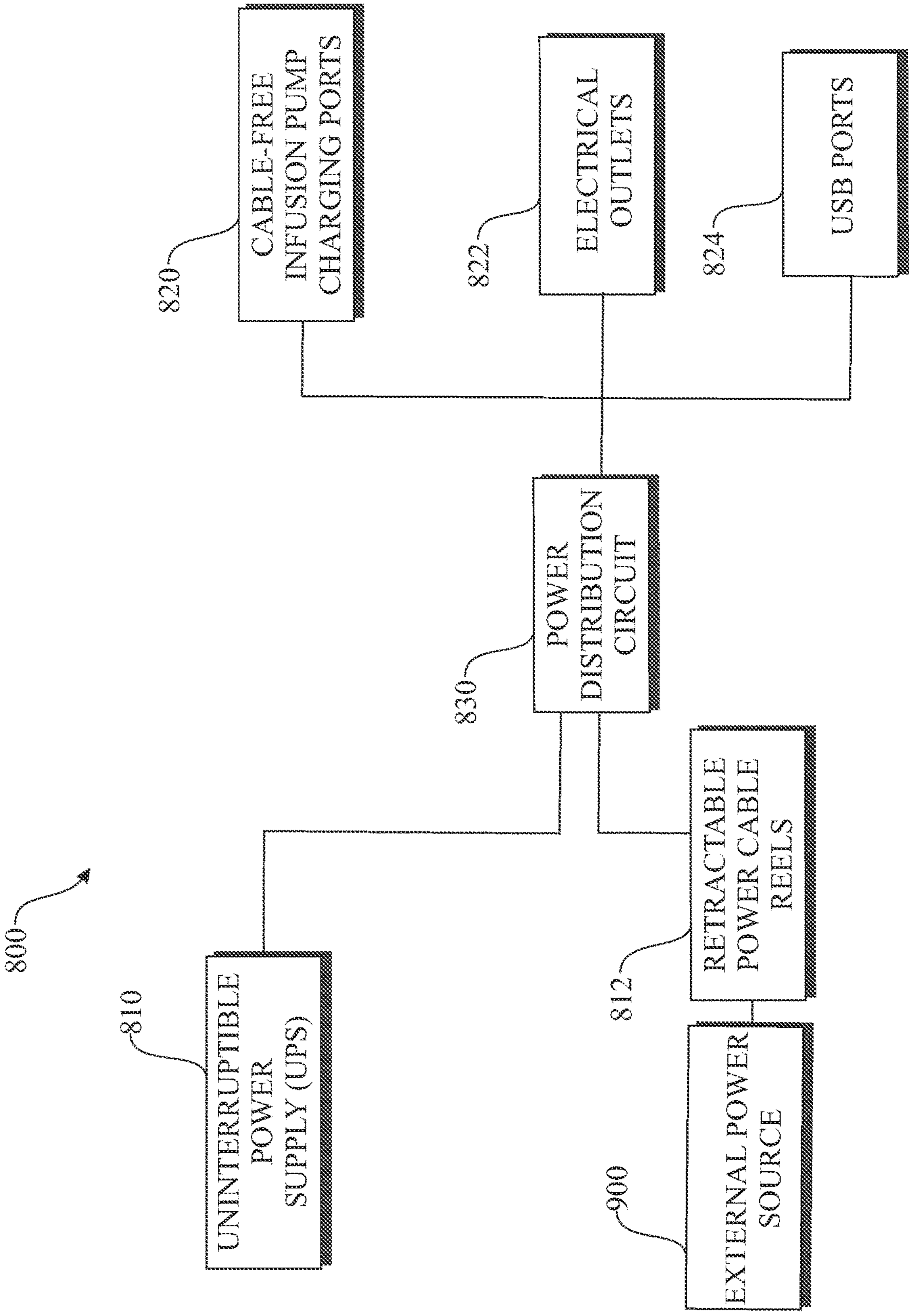
FIG. 8 presents a block diagram illustration of the electrical equipment housed in the pole assembly disclosed in FIGS. 1-7.

Referring now to FIG. 8, a block diagram 800 is shown describing the network of electrical equipment housed in assembly 100, according to one aspect of the present invention. At the power input side, the uninterruptible power supply (UPS) component 810 encompasses the UPS device housed in UPS unit 140 of assembly 100, as shown in the figures. The retractable power reels component 812 encompasses the retractable cable reel 292 carried by the wheeled base subassembly 130 (including the top-exiting retractable electrical plug 224 emerging from the top end 226 of central vertical pole 116) and the retractable cable reel (not visible) housed, for example, in the upper compartment 146 of housing 142 of UPS unit 140 (including the bottom-exiting retractable electrical plug emerging from the rear side 174 of base cover 160). The top-exiting and/or bottom-exiting electrical plugs associated with the retractable cable reels component 812 housed in assembly 100 are electrically connected to convenient outlets in the ambient environment (e.g., ceiling outlet or wall outlet in an operating room or care facility), which establish power connections to an external power supply 900. At the power input side, then, power is delivered by the onboard UPS component 810 or by the external power source 900 via connection using the retractable power cable reels component 812. At the power output side, power is delivered to various devices housed in assembly 100, including, but not limited to, charging ports 820 for the cable-free infusion pumps 700 mounted on the pivotable arms of the rack-forming arm subassembly 402 (corresponding to the set of charging brackets 470), electrical outlets 822, and USB ports 824. The electrical outlets 822 include, for example, the outlets forming part of the electrical panel or console 240 of electrical assembly 236 of lower portion 110 at the UPS housing 142 (FIG. 2), and the outlets 462 forming part of the rear electrical panel 460 of middle portion 112 at the rear side of carrier subassembly 126 (FIG. 2). The USB ports 824 include, for example, the USB ports stationed near the foldable tray 504 at the front side 426 of the hub portion 400 of carrier subassembly 126. A power distribution circuit 830 distributes power from the power input side (i.e., UPS or external power supply) to the power output side (i.e., infusion pump charging ports, electrical outlets, USB ports). Any conventional circuit 830 well known to those skilled in the art can be used to provide this power distribution functionality. The assembly 100 would be equipped with the necessary cabling and/or wiring to communicate and/or route output power from the power distribution circuit 830 to the destination devices or equipment (i.e., infusion pump charging ports, electrical outlets, USB ports). The power distribution circuit 830, for example, can be implemented as a printed circuit board (PCB) installed at any suitable location in assembly 100, such as UPS unit 140 of the lower-level portion 110.

The disclosed smart IV pole 100 may additionally include a remote application or program, an "app", that can control the different devices connected to the smart IV pole 100. The app may be actuated by a wired controller or may be located on a wireless device connected to the different devices by known means. Lastly, the smart IV pole includes sensors for medical device location system for the equipment installed.

Since many modifications, variations, and changes in detail can be made to the described preferred embodiments of the invention, it is intended that all matters in the foregoing description and shown in the accompanying drawings be interpreted as illustrative and not in a limiting sense. Thus, the scope of the invention should be determined by the appended claims and their legal equivalents.

What is claimed is:

1. A stand assembly, comprising:
- a base subassembly;
- a carrier subassembly disposed above the base subassembly;
- an arm subassembly mounted to the carrier subassembly and including one or more arms pivotably connected to the carrier subassembly; and
- an electrical subassembly comprising:
  - one or more charging ports disposed on the arm subassembly;
  - one or more electrical outlets disposed on the base subassembly or the carrier subassembly:
  - one or more mobile device connectors disposed on the base subassembly or the carrier subassembly:
  - one or more retractable power cable reels, each housed in the assembly and having an input plug available to connect to an external power source and an output plug;
  - an uninterruptible power supply; and
  - a power distribution circuit configured to electrically couple the uninterruptible power supply and/or the one or more retractable power cable reels to the one or more charging ports, the one or more electrical outlets, and the one or more mobile device connectors.

2. The stand assembly of claim 1, wherein at least one arm of the arm subassembly is configured to selectively adopt a deployed configuration and a retracted configuration.

3. The stand assembly of claim 1, wherein at least one arm of the arm subassembly is configured in a first mode to pivot about a generally horizontal axis enabling the arm to traverse through a generally vertical plane, and configured in a second mode to pivot about a generally vertical axis enabling the arm to traverse through a generally horizontal plane.

4. The stand assembly of claim 3, wherein the first mode facilitates retraction of the arm into a generally vertical orientation and facilitates extension of the arm into a generally horizontal orientation.

5. The stand assembly of claim 1, further comprising:
- an upper-level third subassembly comprising:
  - a vertical pole mounted to the base subassembly; and
  - a cross-bar rack device mounted to the vertical pole.

6. The stand assembly of claim 5, wherein the cross-bar rack device further comprises:
- a right side telescoping device mounted to a hub device, wherein the hub device is mounted to the vertical pole;
- a left side telescoping device mounted to the hub device;
- at least one hook disposed on the right side telescoping device or the left side telescoping device.

7. The stand assembly of claim 1, wherein the base subassembly further comprises:
- a wheeled base subassembly; and
- a cover configured to cover the wheeled base subassembly.

8. The stand assembly of claim 7, further comprises a brake system configured to apply a braking action to the base subassembly.

9. The stand assembly of claim 8, wherein the brake system comprises:
- a brake element; and
- a user-actuatable mechanism configured to move the brake element between a braking position in which the brake element is disposed in contacting engagement with a ground surface, and a release position in which the brake element is disengaged from the ground surface.

10. The stand assembly of claim 1, further comprises:
- a device configured to emit a signal that indicates a location of the assembly;
- a loading configuration adoptable by the assembly in which one or more medical devices mounts to one or more arms of the arm subassembly; and
- at least one location indicator each associated with a respective one of the one or more medical devices mounted to the one or more arms of the arm subassembly.

11. The stand assembly of claim 1, wherein the base subassembly comprises:
- a wheeled base subassembly, and
- a cover configured to cover the wheeled base subassembly,
  - wherein the cover includes an upper side and a sidewall extending from the upper side, and
  - wherein at least one arm of the arm subassembly includes one or more charging ports.

12. The stand assembly of claim 1, wherein the base subassembly comprises:
- a wheeled base subassembly; and
- a cover configured to cover the wheeled base subassembly,
  - wherein the cover includes an upper side and a lateral structure extending from the upper side; and
  - wherein at least one arm of the arm subassembly is configured to pivot about a generally horizontal axis enabling the arm to traverse through a generally vertical plane and to move between a retracted position and an extended position, and further configured to pivot about a generally vertical axis enabling the arm to traverse through a generally horizontal plane.

13. The stand assembly of claim 1, wherein the base subassembly comprises:
- a wheeled base subassembly;
- a brake system configured to apply a braking action to the base subassembly; and
- a cover configured to cover the wheeled base subassembly and at least part of the brake system,
  - wherein at least one arm of the arm subassembly is configured to pivot about a generally horizontal axis enabling the arm to traverse through a generally vertical plane and to move between a retracted position and an extended position, and further configured to pivot about a generally vertical axis enabling the arm to traverse through a generally horizontal plane.

14. The stand assembly of claim 1, wherein the base subassembly comprises:
- a wheeled base subassembly;
- a brake system configured to apply a braking action to the base subassembly;
- a cover configured to cover the wheeled base subassembly and at least part of the brake system, wherein at least one arm of the arm subassembly is configured to selectively pivot and adopt a deployed configuration and a retracted configuration; and an upper-level third subassembly comprising:

a vertical pole mounted to the base subassembly; and a cross-bar rack device mounted to the vertical pole, wherein the cross-bar rack device comprises:

a right side telescoping device mounted to a hub device, wherein the hub device is mounted to the vertical pole; and a left side telescoping device mounted to the hub device.

15. A stand assembly, comprising:

a base subassembly including:

a wheeled base subassembly;

a brake system configured to apply a braking action to the wheeled base subassembly; and a cover configured to cover the wheeled base subassembly and at least part of the brake system, wherein the cover includes an upper side, a sidewall extending from the upper side, and a front opening in the sidewall to enable access to the brake system;

a upper-level third subassembly comprising:

a vertical pole mounted to the base subassembly; and a cross-bar rack device mounted to the vertical pole, wherein the cross-bar rack device comprises:

a right side telescoping device mounted to a hub device, wherein the hub device is mounted to the vertical pole;

a left side telescoping device mounted to the hub device;

a carrier subassembly disposed above the base subassembly;

an arm subassembly mounted to the carrier subassembly and including one or more arms pivotably connected to the carrier subassembly;

wherein at least one arm of the arm subassembly is configured to selectively adopt a deployed configuration and a retracted configuration;

wherein at least one arm of the arm subassembly includes one or more charging ports; and one or more charging brackets disposed on the arm subassembly.

16. A stand assembly, comprising:

a device configured to emit a signal indicating a location of the stand assembly;

a base subassembly including:

a wheeled base subassembly;

a brake system configured to apply a braking action to the wheeled base subassembly;

wherein the brake system includes a brake element and further includes a mechanism configured to move the brake element between a braking position in which the brake element is disposed in contacting engagement with a ground surface, and a release position in which the brake element is disengaged from the ground surface, and a cover configured to cover the wheeled base subassembly and at least part of the brake system, wherein the cover includes an upper side, a sidewall extending from the upper side, and a front opening in the sidewall to enable access to the brake system;

an upper-level third subassembly comprising:

a vertical pole mounted to the base subassembly; and a cross-bar rack device mounted to the vertical pole, wherein the cross-bar rack device comprises:

a right side telescoping device mounted to a hub device, wherein the hub device is mounted to the vertical pole;

a left side telescoping device mounted to the hub device;

a carrier subassembly disposed above the base subassembly;

a support subassembly configured to support the carrier subassembly and including one or more support posts;

an arm subassembly mounted to the carrier subassembly and including one or more arms pivotably connected to the carrier subassembly, wherein at least one arm of the arm subassembly is configured to pivot about a generally horizontal axis enabling the arm to traverse through a generally vertical plane in a range of movements including a retracted position and an extended position, and further configured to pivot about a generally vertical axis enabling the arm to traverse through a generally horizontal plane, and wherein at least one arm of the arm subassembly includes one or more charging ports;

one or more charging brackets each incorporating a respective one of the one or more charging ports; and an electrical subassembly comprising:

one or more electrical outlets disposed on the base subassembly and/or the carrier subassembly;

one or more mobile device connectors disposed on the base subassembly and/or the carrier subassembly;

one or more retractable power cable reels each having an input plug available to connect to an external power source and an output plug;

an uninterruptible power supply; and a power distribution circuit configured to electrically couple the uninterruptible power supply and/or the one or more retractable power cable reels to the one or more charging ports, the one or more electrical outlets, and the one or more mobile device connectors, wherein the assembly adopts a loading configuration in which one or more medical devices mounts to the one or more mounting brackets on the arm subassembly, and in which one or more containers hang from the rack subassembly.

* * * * *